United States Patent [19]

Bachman

[11] Patent Number: 4,467,324
[45] Date of Patent: Aug. 21, 1984

[54] APPARATUS AND METHOD FOR PRINTING ANNOTATED ELECTROCARDIAL DATA

[75] Inventor: John A. Bachman, Dana Point, Calif.
[73] Assignee: Del Mar Avionics, Irvine, Calif.
[21] Appl. No.: 403,356
[22] Filed: Jul. 3, 1982

Related U.S. Application Data

[63] Continuation of Ser. No. 163,777, Jun. 27, 1980, abandoned.

[51] Int. Cl.³ .................................................. G09G 1/00
[52] U.S. Cl. ...................................... 340/722; 315/386; 340/745; 340/734; 346/33 ME; 346/110 R
[58] Field of Search ............... 346/33 ME, 33 R, 23, 346/110 R, 110 VT; 315/386, 392; 340/721, 722, 745, 734, 742

[56] References Cited

U.S. PATENT DOCUMENTS

| | | | |
|---|---|---|---|
| 2,812,472 | 11/1957 | Welliver | 315/386 |
| 3,427,541 | 2/1969 | Middleton | 340/734 |
| 3,624,632 | 11/1971 | Ophir | 315/392 |
| 3,698,004 | 10/1972 | Lone | 346/110 R |
| 3,721,856 | 3/1973 | Dick | 315/392 |
| 3,754,277 | 8/1973 | Lowe | 346/110 R |
| 3,886,526 | 5/1975 | Smith | 346/110 R |
| 3,976,991 | 8/1976 | Hickin | 340/742 |
| 4,088,990 | 5/1978 | Sass | 346/110 R |
| 4,094,310 | 6/1978 | McEachern et al. | 346/33 ME |

Primary Examiner—Marshall M. Curtis
Attorney, Agent, or Firm—Beehler, Pavitt, Siegemund, Jagger & Martella

[57] ABSTRACT

A single-beam CRT printer, used as a validator record of electrocardiographic data played back from a magnetic tape at a much higher speed than the speed at which it was recorded, includes a scan circuit for generating signals for steering the beam alternately through an ECG scan pattern and through a character scan pattern and further includes a character generator for modulating the intensity of the beam in relation to the instantaneous location of the beam within the character scan pattern to cause the beam to print characters, the intensity of the beam and its linear velocity being increased during execution of the character scan pattern to permit the characters to be printed at such a high speed that only an insignificant part of the ECG plot is omitted while the characters are being printed.

6 Claims, 3 Drawing Figures

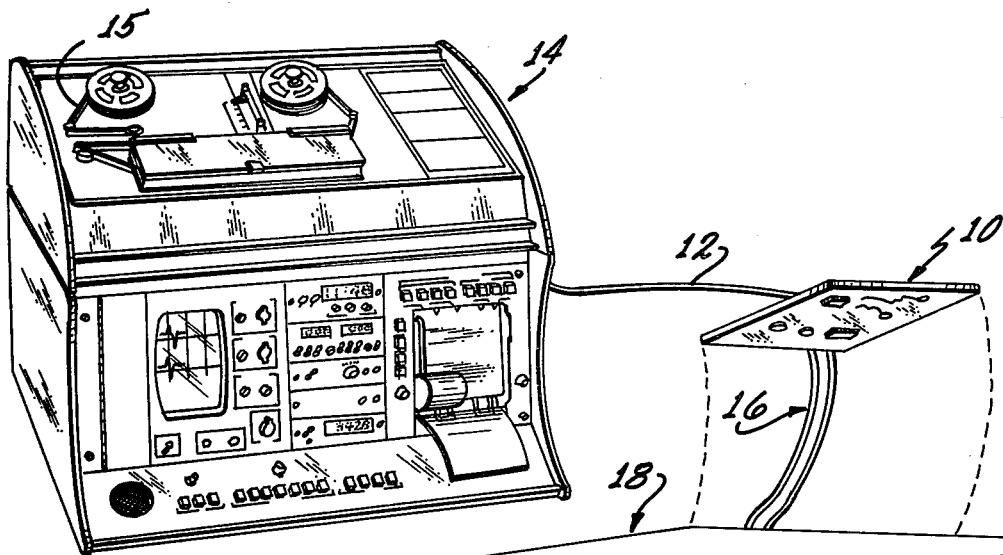
Fig. 1
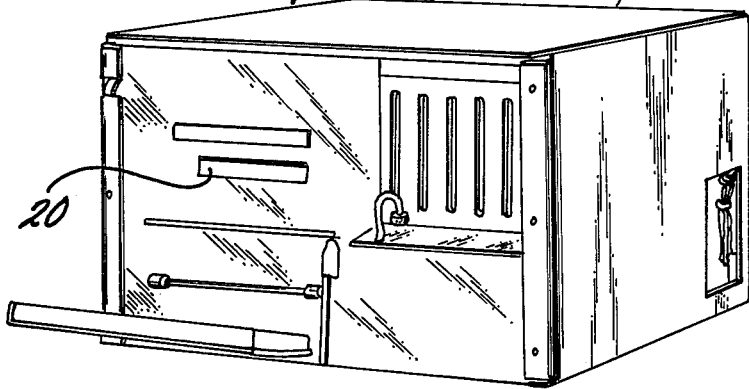
Fig. 2
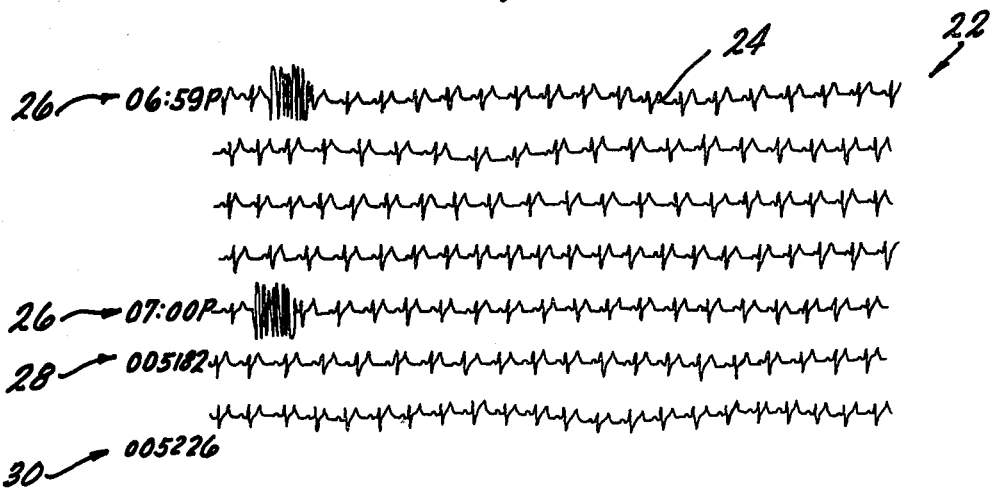

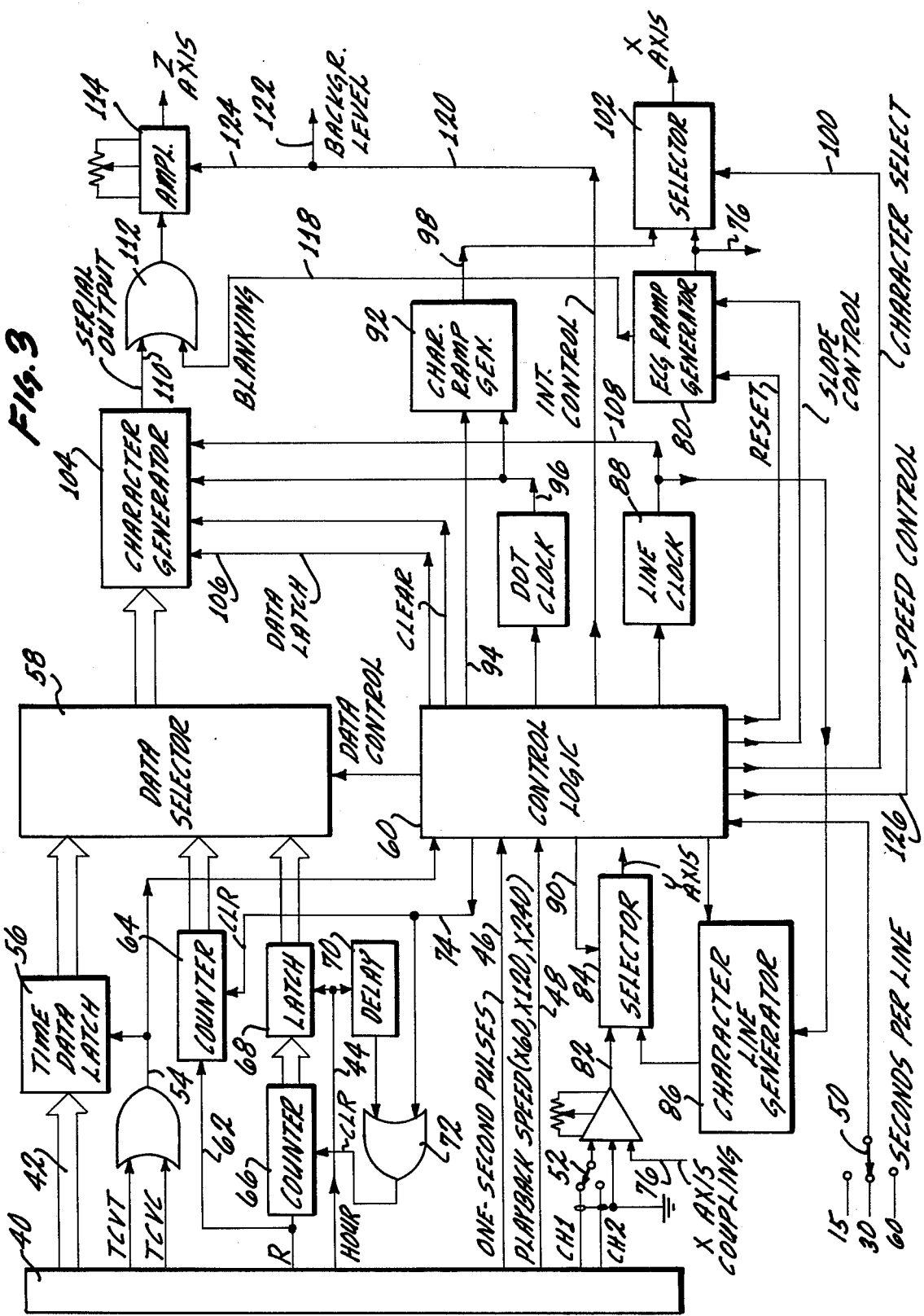

4,467,324

APPARATUS AND METHOD FOR PRINTING ANNOTATED ELECTROCARDIAL DATA

This is a continuation of application Ser. No. 163,777, filed June 27, 1980, now abandoned.

BACKGROUND OF THE INVENTION

1. Field of the Invention

The present invention is in the field of cardiography, and more particularly relates to apparatus for producing at a high speed a printed record of electrocardiographic data played back from a magnetic tape at a much higher speed than the speed at which it was recorded.

2. The Prior Art

In ambulatory monitoring as currently practiced, the patient is outfitted with instruments for sensing electrocardial signals and with a small lightweight portable magnetic tape recorder for recording the sensed signals as the patient engages in various activities over an extended period of time, which may be as long as 26 hours. Following the recording session, the recorded magnetic tape is brought to a central facility where the recorded signals are studied to ascertain information about the behavior of the patient's heart.

Various types of equipment may be available at the central facility to facilitate study of the signals derived from the magnetic tape. At the minimum, a playback apparatus is required to reproduce the signals recorded on the tape. If necessary, the validator of the present invention can operate on signals produced by a relatively simple playback unit.

Another type of equipment typically used at the central facility is a playback-analyzer, which incorporates in a single unit of equipment both apparatus for playing back the tape and further includes circuitry for recognizing, counting, measuring, and displaying relevant characteristics of the recorded data signals. The validator of the present invention is preferably used in association with such a playback-analyzer. Such a playback-analyzer is described in U.S. Pat. No. Re. 29,921 for "Electrocardiographic Computer", reissued Feb. 27, 1979 to Cherry et al., and assigned to the assignee of the present invention. The disclosure of U.S. Pat. No. Re. 29,921 is incorporated herein by reference.

As described in U.S. Pat. No. Re. 29,921, the analysis portion of the equipment includes an arrhythmia computer which detects and digitally displays the number of premature ventricular contractions and superventricular ectopic beats, and generates a signal to cause a special mark to be written on the record when the arrhythmia occurrences exceed a predetermined number during a predetermined time interval. The same signal may also be used to slow the playback so that the arrhythmia occurrences can be plotted in real time. The arrhythmia computers include an ability to select one or more parameters to determine the occurrence of an arrhythmia; the parameters include paired beats, prematurity, width, or amplitude. Also, preselected abnormalities in heart function such as abnormal ventricular ectopic beats, superventricular ectopics, ST levels, rapid heart beat, slow heart rate, etc., may be recognized, so that the portion of the recording including the abnormalities can be plotted at real time speed.

The playback-analyzer equipment is not normally used to reproduce in printed form the entire recorded signal, although the equipment is capable of doing this. Instead, the playback-analyzer is normally used to recognize the occurrence of abnormal heart action so as to permit the ECG signals to be reproduced only for the time intervals when the abnormalities occurred. The plotted ECG signals are presented on a strip chart by the playback-analyzer.

The characteristics of the playback-analyzer have been reviewed in some detail so that the distinctions between the playback-analyzer and a validator can be seen more clearly and their complementary functions better understood.

As the word "validator" is currently used, it refers to a piece of equipment which enables an operator to verify the output of the analyzer portion of the playback-analyzer, e.g., to provide an independent check on the number of abnormalities of a particular type that have been recognized by the analyzer. In addition to, and in support of this basic function, validators typically are able to produce at very high speed a plot of the entire recorded ECG signal. Ideally, this complete record is formatted to facilitate visual detection of irregularities by the operator. The use of a well-designed format permits the operator to scan rapidly through the data, which typically might be printed on a dozen pages. The operator, based on his experience, recognizes the occurrences of abnormal heart action, and counts them, thus providing a completely independent check on the operation of the analyzer.

Several validators are known in the prior art. One such validator is disclosed in co-pending U.S. patent application Ser. No. 088,105 filed Oct. 24, 1979 for "Validator for Electrocardial Data Processing System", which is assigned to the assignee of the present invention. The validator described therein employs two memories, so that as one of the memories is receiving data from a playback apparatus, data is being supplied by the other memory to a mechanical plotter. The design of this validator assures that no part of the data is omitted from the plotted record, and the time of day is printed at intervals in the margin. The design is relatively sophisticated, and the unit is necessarily more expensive because of the extensive capability that it provides.

Another validator known in the art is the Model No. 7350 produced by AdvanceMed, 17346 Eastman Street, Irvine, Calif. This unit omits a portion of the ECG signal from the plot while the time of day characters are being printed This considerably reduces its value for use in verifying the accuracy of other equipment.

Thus, a need was recognized for a validator less expensive than that disclosed in the aforementioned U.S. patent application Ser. No. 088,105, but more accurate than the Model 7350 made by AdvanceMed. Cost considerations preclude the use of the dual memory technique, and suggest the use of a single-beam printer. However, it was by no means clear how a single beam could be employed to print the time-of-day characters without omitting a significant portion of the ECG signal. Multiplexing of the single beam was considered, but did not appear to be a feasible approach because of the high-beam scan rates required and the attendant reduction in brightness. A new approach was needed to satisfy the design requirements at minimal cost.

SUMMARY OF THE INVENTION

The present invention embodies a new design approach in which high accuracy is achieved at a moderate cost. A single-beam CRT is used to write successively the time-of-day characters and the ECG signal, but the amount of ECG signal that is omitted while the time-of-day characters are being written has been reduced to an insignificant fraction of one heart beat. This has been accomplished by greatly speeding up the scan rate of the beam while the time-of-day characters are being written, so that the time-of-day characters are written during a time interval considerably less than the duration of a single heart beat.

Normally, the tremendous increase in the beam scanning speed while the time-of-day characters are being written would result in those characters being unacceptably lacking in intensity and perhaps not visible at all. This problem has been overcome in the present invention by greatly increasing the beam intensity while the time-of-day characters are being written. In a preferred embodiment, this is accomplished by greatly augmenting the gain of the Z-axis amplifier when the time-of-day characters are being printed.

In addition to its normal use in validating the accuracy of a playback-analyzer, the validator of the present invention can also be used as a printer in conjunction with an appropriate playback unit to produce at high speeds a printed record of signals recorded on a magnetic tape.

In a preferred embodiment, the validator includes means by which the operator can select the number of seconds of patient time that are to be written on each line of the record. In the preferred embodiment, this choice of the number of seconds of patient time data to be printed on each line may be made independently of the playback speed.

In the preferred embodiment, each new minute of printed data begins on a new line, and the time of day is recorded on the record in the left hand margin, adjacent to but spaced from the left end of the line. The printed time-of-day characters make it possible for the operator to determine within a few seconds the time of day at which an observed irregularity in the heart action occurred. This, in turn, is useful in correlating the irregularity with the activity of the patient at that time, and further serves as an index to the location of the observed irregularity on the magnetic tape.

In a preferred embodiment, the validator includes means for counting the number of R-waves that occur during each hour and for printing out on the hour the hourly total on the row immediately below the time characters which identify the start of a new hour. Also, in the preferred embodiment, the number of R-waves on the entire tape is counted and printed at the end of the printed record in the left hand margin. The R-wave totals are helpful in diagnosis and can be correlated, at least hourly, with the activities of the patient.

The novel features which are believed to be characteristic of the invention, both as to organization and method of operation, together with further objects and advantages thereof, will be better understood from the following description considered in connection with the accompanying drawings, in which a preferred embodiment of the invention is illustrated by way of example. It is to be expressly understood, however, that the drawings are for the purpose of illustration and description only, and are not intended as a definition of the limits of the invention.

BRIEF DESCRIPTION OF THE DRAWINGS

FIG. 1 is a perspective view showing the validator of the present invention connected to a playback-analyzer for use;

FIG. 2 is a facsimile of a portion of a chart produced by the validator of the present invention; and, FIG. 3 is a block diagram of the control unit used in a preferred embodiment of the invention to control the operation of the plotter.

DETAILED DESCRIPTION OF THE PREFERRED EMBODIMENT

As shown in FIG. 1, the present invention is implemented by a control circuit 10 which is physically integrated into a printer 18. The control circuit 10 is connected by the wires 16 to the CRT of the printer, and is connected by the cable 12 to the playback-analyzer unit 14. In a preferred embodiment the playback-analyzer unit 14 is an instrument of the type described in the aforementioned U.S. Pat. No. Re. 29,921, reissued Feb. 27, 1979 to Cherry et al.

That instrument includes a magnetic tape playback system in which recorded electrocardiographic signals recorded on a magnetic tape 15 are converted to electrical signals when the tape is played back at a much higher speed than the speed at which the tape was recorded. Typical playback speeds are 60, 120, and 240 times the real time speed. At the X240 speed, a taped 24-hour ambulatory monitoring session can be played back and analyzed in only 6 minutes.

The playback-analyzer unit 14 also normally generates a number of other signals in the course of the analysis in addition to the normal two channels of ECG data. The playback-analyzer unit 14 recognizes the occurrence of each R-wave in the ECG signal and generates a pulse upon the occurrence of each R-wave. These successive pulses are applied to the control circuit 10 via the cable 12. The playback and analyzer unit 14 also produce signals indicating the selected playback speed.

Additionally, the playback and analyzer unit 14 generates several types of time signals and clock signals. These include a one-second clock signal, a one-minute clock signal, and a one-hour clock signal. In addition to these clock signals, the playback and analyzer unit 14 also generates in parallel digital form a set of signals which collectively represent the time of day at which the instantaneous ECG signals were recorded. All of the aforementioned signals are applied to the control circuit 10 by the playback-analyzer unit 14. It is the control circuit 10 that oversees the proper placing of the various data items on the recorded chart shown in FIG. 2. The printer 18 includes a cathode-ray tube (CRT) having a single beam which writes on the chart whatever the beam is commanded to write. However, the data signals supplied to the control circuit 10 from the playback-analyzer unit 14 are by no means in a proper form to serve for guiding the beam of the CRT.

In a preferred embodiment, the printer 18 is an oscillographic fiber optic recorder Model LS-6A, manufactured as OEM equipment by the Honeywell Corp. Test Instruments Division of Scarborough, Ontario, Canada. That model uses a cathode-ray tube having a one-half-inch-high by five-inch-wide fiber optic faceplate. The photosensitive recording paper is held in intimate contact with the fiber optic faceplate, eliminating optical components and yielding maximum recording energy transfer. The recorder can produce recordings which are immediately visible, using a wide variety of print-out papers. Recording resolution is excellent, typically exceeding 100 line pairs per inch. The lateral position of the beam is determined by an X-axis signal, and the vertical position of the beam is controlled by a Y-axis signal. The beam is deflected magnetically, and the intensity of the beam is determined by a Z-axis signal that can be modulated at frequencies in excess of 8 MHz. Thus, the control circuit 10 generates the X-axis, Y-axis and Z-axis signals to control the beam of the CRT to write the information provided to the control circuit 10 by the playback-analyzer unit 14 onto the record in a predetermined format. A block diagram of a preferred embodiment of the control circuit 10 is shown in FIG. 3.

After being conducted through the cable 12, the signals provided to the control circuit 10 by the playback analyzer unit 14 pass through the terminal strip 40 of FIG. 3. Those signals include the time-of-day signals on the bus 42 in parallel binary form, which give the current hour and minute along with an AM/PM indicator. For example, the signals on the bus 42 might represent the time of day 06:59P.

The next two signals TCVT and TCVC are mutually exclusive, but one of them is always present. These signals are synch pulses which occur once each minute on the minute.

The control circuit 10 also receives an R-wave signal in the form of a pulse that is produced upon the occurrence of each R-wave.

Additionally, the control circuit is provided with: a signal consisting of a pulse which is produced once each hour on the hour, on the line 44; with a continuing sequence of one-second clock pulses on the line 46; and with a signal on the line 48 which indicates the playback speed.

Finally, the signals received by the control circuit 10 include the two channels of ECG signals as they have been reproduced by playing back the magnetic tape at the X60, X120, or X240 speed.

Before putting the printer 18 into use, the operator must set the switch 52 in accordance with which channel he desires to print, and must also set the switch 50 to establish the number of seconds of real time data that is to be recorded on each line of the chart produced.

The synch signal which occurs once each minute on the minute on line 54 clears the time data latch 56 of the digits identifying the just-elapsed minute, so that the digits identifying the current minute can be held in the latch for use by the data selector 58. The synch signal on the line 54 is also applied to the control logic 60 for use in establishing the times at which the time characters should be printed.

The R-wave pulses received from the playback-analyzer unit 14 are applied via the line 62 to the counter 64, which is used to register the cumulative number of R-waves played back from the tape. In a preferred embodiment of the invention, the cumulative count provided by the counter 64 is printed in the form of characters 30 of FIG. 2 at the end of the recording.

The R-wave signal is also applied to the counter 66 which is used to provide hourly totals of the number of R-waves. At the end of each hour, the signal on the line 44 is used to latch the then-current count of the counter 66 into the latch 68, and the counter 66 is then cleared after a delay introduced by the delay circuit 70. The OR circuit 72 permits the counter 66, as well as the counter 64, to be cleared by a CLEAR signal on the line 74 generated by the control logic 60 as part of the initialization procedure at the beginning of each recording period.

As mentioned above, the switch 52 is used by the operator to select which channel of the ECG signals he wishes to plot. The selected signal is then combined with an X-axis coupling signal on the line 76 in the amplifier 78. The purpose of the X-axis coupling is to provide a steadily increasing upward bias to the ECG signals as they are traced across the page to compensate for the downward motion of the recording paper with respect to a horizontal line across the face of the CRT. In the preferred embodiment of FIG. 3, the X-axis coupling signal is the output of the ECG ramp generator 80 which determines the X displacement of the beam when a line of ECG signals is being printed. The amount of bias applied to the ECG signal is proportional to the signal on the line 76, and the proportionality constant is related to the speed of the recording paper. The biased ECG signal is then applied to the line 82.

Also applied to the selector 84 is a signal from the character line generator 86. This second signal is generated when the time-of-day or heart-rate characters are being printed. These characters are printed in a raster-scan mode, wherein the beam is caused to trace successive vertically-spaced rows of fixed duration. The duration of the rows is established by the line clock 88 in response to a control signal from the control logic 60. The control logic 60 initiates the generation of each line by applying a control signal to the line clock 88 and to the character line generator 86. In response to the control signal, the line clock 88 generates a sequence of clock pulses which are accumulated by the character line generator 86 to produce the ever-increasing heights of the lines in the raster scan. The control logic 60 applies a control signal via the line 90 to the selector 84 to determine whether characters or ECG signals will be printed.

As mentioned above, when the ECG signal is being plotted, the X-axis (horizontal) location of the beam is determined by the ECG ramp generator 80 which generates successive sawtooth waveforms corresponding to the successive rows of ECG data to be printed on the recording. Similarly, the character ramp generator 92 controls the horizontal location of the beam when the characters are being written. After being initialized by a control signal on the line 94, the character ramp generator 92 integrates the clock pulses produced on the line 96 by the dot clock to produce a signal on the line 98 representing the desired horizontal location of the beam. A control signal on the line 100 is applied to the selector 102 by the control logic 60 for determining whether the ECG ramp signal on the line 76 or the character ramp signals on the line 98 will be applied to the X-axis of the CRT.

The data selector 58, under the control of the data control signal applied by the control logic 60 selects the data items that are to be printed in character form: the time of day, the total R-waves that occurred in the preceding hour, and the total number of R-waves that have occurred in the entire run. The selected data are latched into the character generator 104 by a data latch control signal produced on the line 106 by the control logic 60. This tells the character generator 104 which characters are to be printed, and it remains for the character generator 104 to produce a serial output on the line 110 that will cause the beam of the CRT to generate the selected characters.

In a preferred embodiment, a raster scan is used to generate the characters. Six characters are always produced at a time. Each character is developed on a standard 5×7 dot matrix by modulating the beam intensity between two levels representing black and white. Thus, the raster swept by the beam in printing the six characters is 7 lines high and 30 dots in width. To enable the character generator 104 to know where the beam is located at some instant during the scanning process, the dot clock signal on the line 96 and the line clock signal on the line 108 are applied to the character generator 104. From the clock signals, the character generator 104 can determine the location of the beam at any instant in the scanning process, and the character generator 104 can then determine whether the selected character group is either "white" or "black" at that particular location. This process is repeated at successive beam locations to produce a serial output for modulating the intensity of the beam, i.e., Z-axis control. The serial output produced by the character generator 104 on the line 110 is applied through the OR gate 112 and the amplifier 114 to the Z-axis input of the CRT.

In a preferred embodiment, the character generator 104 is a component manufactured by National Semiconductor.

In accordance with the present invention, the control logic 60 generates an intensity control signal on the line 120 for use in altering the gain of the amplifier 114 so as to greatly increase the intensity of the beam when the data characters are being produced. From FIG. 2 it is seen that the time-of-day characters 26 are produced at the beginning of each minute of real time, that the characters 28 representing the number of R-waves within the most recent hour are printed on the row immediately below the first row printed in the new hour, and the characters 30 representing the total accumulated R-waves are printed only at the end of the record. The control logic 60 therefore utilizes the one-minute synch signal on the line 54 to determine the time for printing the time-of-day characters 26. Likewise, the control logic 60 utilizes the hour signal on the line 44 to determine when to print the characters 28. Finally, the control logic 60 recognizes the cessation of the one-second pulses on the line 46 as indicating the end of the recording and consequently the time for printing the characters 30. The control logic 60 counts the number of one-second pulses on the line 46 following each of the one-minute synch pulses on the line 54 to determine when the required number of seconds of data have been plotted on a particular row.

The ECG ramp generator 80 generates a blanking signal on the line 118 during the retrace portion of the sawtooth ramp so that the retrace motion of the beam will not be printed.

As described above, the control logic determines from the synch signal on line 54 and the hour signal on the line 44 and from the one-second pulses on the line 46 when a raster scan is to be initiated for printing the characters. Using a singlebeam CRT and without multiplexing the beam, it is not possible to print both the characters and the ECG signals simultaneously. Accordingly, it is highly desirable that the interruption of the printing of the ECG signals in order to print the characters should be minimized. One way of minimizing the interruption is to move the beam at an extremely fast speed during the raster scan that is used to print the characters. However, merely moving the beam faster does not produce the desired result, because at the higher beam speeds, the brightness of the trace produced by the beam on the face of the CRT is greatly diminished and may fall below the level of brightness required to produce any mark on the recording paper.

This dilemma is solved in the present invention by the control logic 60 which generates a special intensity control signal on the line 120. This signal selectively alters the gain of the amplifier 114 so that the gain is raised to a high level when characters are to be printed, but is reduced to a low level when the ECG signal is to be plotted.

In the particular embodiment of the invention as shown in FIG. 3, the amplifier 114 has only a limited dynamic range for high-frequency input. In other words amplifier 114 has a low frequency roll-off such that only the high frequency signals are amplified. Accordingly, the intensity control signal on the line 120 is divided into a low-frequency background level on the line 122 and a high-frequency component on 14 the line 124. Both the background level signal on the line 122 and the output of the amplifier 114 are applied to the CRT to modulate the intensity of the beam.

The control logic 60 also generates a speed control signal on the line 126 for controlling the speed of the advancing recording paper in proper relation to the playback speed signal on the line 48 and the selected number of seconds of data to be plotted on each line, in accordance with the setting of the switch 50. It should be noted in this connection, that the recorder of the present invention includes no provision for storing of the data to be printed. Instead, the data is printed as fast as it arrives.

Thus, there has been described a printer for printing ECG signals in successive rows and for printing in the margin adjacent to but spaced from the rows of characters representing the time of day and the number of R-waves that have occurred. This result is achieved in a single-beam printer in which the intensity of the beam is greatly increased when the characters are being printed so that the time required for printing the characters can be held to a minimum, thereby minimizing the amount of ECG date that is omitted from the print while the characters are printed.

Although the present invention is primarily intended for use in validating the results obtained from a playback-analyzer that independently recognizes and counts various types of coronary irregularities, it should be recognized that the present invention can also be used simply as a plotter capable of producing characters at selected locations on a chart.

The foregoing detailed description is illustrative of one embodiment of the invention, and it is to be understood that additional embodiments thereof will be obvious to those skilled in the art. The embodiments described herein, together with those additional embodiments, are considered to be within the scope of the invention.

What is claimed is:

1. In a high speed data playback CRT printer having a single beam and an X and Y drive circuit of the type used to plot an applied, analog, ECG signal on a recording medium, and improvement for intermittently also printing on the recording medium, at times determined by an applied timing signal, characters represented by applied character signals and for printing the characters at such a high speed that only an insignificantly small part of the analog ECG plot is omitted while the characters are being printed, said improvement comprising:

scan circuit means for generating in response to an applied scan select signal an analog ECG scan signal and a raster character scan signal and for applying the analog ECG scan signal in an X-Y trace and the character scan signal in a raster trace to the CRT to alternately steer the beam through respectively an ECG scan X-Y tracing pattern at a first linear speed and through a character scan raster pattern at a second linear speed at least several times the first linear speed;

character generator means for modulating the intensity of the beam in relation to the instantaneous location of the beam within the character scan raster pattern and in relation to the applied character signals to cause the beam to print the characters, said character generator means responsive to an applied intensity control signal to maintain the intensity of the beam at a first level while the analog ECG signal is being traced to an X-Y plot and to increase the intensity of the beam when the characters are being traced in a raster scan to a second level at least several times greater than the first level to prevent diminution of intensity when it moves at the second linear speed; and, control means connected to said scan circuit means and responsive to the applied timing signal for generating the scan select signal applied to said scan circuit means, and connected to the CRT for selectively passing the CRT the applied analog ECG signal when the beam is being steered through the ECG scan X-Y tracing pattern for generating the intensity control signal in relation to the applied timing signal, and further connected to said character generator means for applying thereto the intensity control signal.

2. The apparatus of claim 1 wherein said character scan raster pattern is a dot-matrix raster trace and the speed of horizontal tracing of said raster character scan signal is controlled by said control means with a dot clock included therein set at a first rate to step through said dot-matrix raster trace; and wherein the speed of horizontal tracing of said analog ECG scan signal is controlled by said control means with an ECG ramp generator included therein set at a second rate to sweep through said X-Y trace, said first rate of stepping through said dot-matrix trace being substantially greater than said second rate of sweeping through said X-Y trace, said intensity control signal generated by said control means being selectively applied to said scan circuit means to intensify said beam when said beam is being stepped through said dot-matrix trace.

3. The apparatus claim 2 wherein said said speed of horizontal trace of said raster character scan signal is controlled by said control means by integration of said dot clock by a character ramp generator included within said control means and applied to said X drive circuit of said CRT printer.

4. The apparatus of claim 1 wherein said X and Y drive circuits of said CRT printer are controlled by separate circuitry included within said control means for independently horizontally and vertically driving said single beam in a first horizontal and vertical trace in a dot-matrix raster scan at a fast first rate of speed and then independently horizontally and vertically driving said single beam in a second horizontal and vertical trace in an X-Y scan at a slow rate of speed.

5. The apparatus of claim 4 wherein said circuitry for driving said single beam in a dot-matrix trace includes a dot clock for stepping through said horizontal trace, a character ramp generator coupled to said dot clock to generate a horizontal ramp signal to apply to said X drive circuit of said CRT printer, a character generator coupled to said dot clock for selectively generating a serial output indicative of those dots in each horizontal row of said dot-matrix trace to be illuminated, a line clock for generating a signal indicative of each row to be stepped through in said dot-matrix trace, a character line generator coupled to said line clock for generating a vertical stepping ramp signal to apply to said Y drive circuit of said CRT printer, a beam intensification circuit coupled to and responsive to said character generator and to a beam intensity control signal, a control logic circuit coupled to said beam intensification circuit for generating said beam intensity control signal when said dot-matrix trace is to be generated, said beam intensification circuit controlling the intensity of said beam of said CRT printer.

6. The apparatus of claim 5 wherein said circuitry for driving said single beam in an X-Y trace includes an ECG ramp generator for driving said X drive circuit of said CRT printer and wherein said analog ECG signals drive said Y drive circuit of said CRT printer; and, wherein said X and Y drive circuits are selectively coupled between said circuitry for driving said beam in a dot-matrix trace and X-Y trace by control logic circuit, whereby characters are printed in said dot-matrix trace at a substantially greater speed than and independently from said ECG signal without loss of apparent intensity and appreciable loss of said ECG signal.

* * * * *